(12) United States Patent
Sharratt et al.

(10) Patent No.: US 9,096,489 B2
(45) Date of Patent: Aug. 4, 2015

(54) PROCESS FOR PREPARING 3,3,3-TRIFLUOROPROPENE

(75) Inventors: Andrew Paul Sharratt, Cheshire (GB); Claire McGuinness, Cheshire (GB)

(73) Assignee: Mexichem Amanco Holding S.A. de C.V. (MX)

( * ) Notice: Subject to any disclaimer, the term of this patent is extended or adjusted under 35 U.S.C. 154(b) by 0 days.

(21) Appl. No.: 13/256,077

(22) PCT Filed: Apr. 9, 2010

(86) PCT No.: PCT/GB2010/000725
§ 371 (c)(1),
(2), (4) Date: Dec. 6, 2011

(87) PCT Pub. No.: WO2010/116150
PCT Pub. Date: Oct. 14, 2010

(65) Prior Publication Data
US 2012/0071699 A1 Mar. 22, 2012

(30) Foreign Application Priority Data
Apr. 9, 2009 (GB) .................................. 0906191.2

(51) Int. Cl.
*C07C 17/25* (2006.01)
*C07C 17/20* (2006.01)

(52) U.S. Cl.
CPC ............... *C07C 17/206* (2013.01); *C07C 17/25* (2013.01); *C07C 17/20* (2013.01)

(58) Field of Classification Search
USPC ........................................................ 570/158
See application file for complete search history.

(56) References Cited

U.S. PATENT DOCUMENTS

| | | | |
|---|---|---|---|
| 2,889,379 A | 6/1959 | Ruh et al. | |
| 2,918,501 A | 12/1959 | Brehm et al. | |
| 2,931,840 A | 4/1960 | Marquis | |
| 2,996,555 A | 8/1961 | Rausch | |
| 3,000,979 A | 9/1961 | Gibbs | |
| 3,398,204 A | 8/1968 | Gallant | |
| 3,674,665 A | 7/1972 | Cristol et al. | |
| 3,739,036 A | 6/1973 | Valicenti et al. | |
| 3,793,229 A | 2/1974 | Groppelli et al. | |
| 4,093,670 A | 6/1978 | Ozawa et al. | |
| 4,220,608 A | 9/1980 | Feiring | |
| 4,465,786 A | 8/1984 | Zimmer et al. | |
| 4,798,818 A | 1/1989 | Baizer et al. | |
| 5,679,875 A | 10/1997 | Aoyama et al. | |
| 5,811,603 A | 9/1998 | Elsheikh | |
| 5,895,825 A * | 4/1999 | Elsheikh et al. | 570/167 |
| 5,986,151 A | 11/1999 | Van Der Puy | |
| 6,111,150 A | 8/2000 | Sakyu et al. | |
| 6,329,559 B1 | 12/2001 | Sievert et al. | |
| 6,403,524 B2 * | 6/2002 | Scott et al. | 502/307 |
| 2005/0038302 A1 | 2/2005 | Hedrick et al. | |
| 2006/0122441 A1 | 6/2006 | Tung | |
| 2007/0004585 A1 | 1/2007 | Amos et al. | |
| 2007/0112230 A1 | 5/2007 | Mukhopadhyay et al. | |
| 2007/0129579 A1 | 6/2007 | Wang et al. | |
| 2007/0197842 A1 | 8/2007 | Mukhopadhyay et al. | |
| 2008/0230738 A1 * | 9/2008 | Minor et al. | 252/67 |

FOREIGN PATENT DOCUMENTS

| | | | |
|---|---|---|---|
| CN | 1488614 A | * | 4/2004 |
| CN | 1488614 A | | 4/2004 |
| CN | 1651137 A | * | 8/2005 |
| CN | 1651137 A | | 8/2005 |
| CN | 101074185 A | | 11/2007 |
| CN | 101074185 A | * | 11/2007 |
| DE | 1140928 B | | 12/1962 |
| DE | 2128341 | | 12/1971 |
| EP | 0270 006 B1 | | 2/1991 |
| EP | 0319 153 B1 | | 7/1992 |
| EP | 0 436 989 B1 | | 3/1995 |
| EP | 0644 173 A1 | | 3/1995 |
| EP | 0502 605 B1 | | 7/1996 |
| EP | 0 726 243 A1 | | 8/1996 |
| EP | 077 3061 A1 | | 5/1997 |
| EP | 0 957 074 B1 | | 2/2003 |
| EP | 0 939 071 B1 | | 7/2003 |
| EP | 1 350 564 A1 | | 10/2003 |
| FR | 2342952 | | 9/1977 |
| GB | 1 407696 | | 9/1975 |
| WO | WO 93/04025 | | 3/1993 |
| WO | WO 97/05089 | | 2/1997 |
| WO | WO 98/10862 | | 3/1998 |

(Continued)

OTHER PUBLICATIONS

He, F. et. al. Method for preparation of 3,3,3-trifluoropropene CN101074185—English.*
Fang, H. et. al. Preparation of 3,3,3-trifluroropropylene CN1488614—English.*
Lu, J. et al. Patent No. CN1651137; English translation.*
He, F. et al. Patent No. CN101074185; Published on Nov. 21, 2007; English translation.*
Banks, et al., "Preparation of 2,3,3,3-tetrafluoropropene from trifluoroacetylacetone and sulphur tetrafluoride", Journal of Fluorine Chemistry, vol. 82, pp. 171-174, 1997.
Buchner, et al., "Reactions of Gaseous, Halogenated Propene Radical Cations with Ammonia: A Study of the Mechanism by Fourier Transform Ion Cyclotron Resonance", Chem. A. Eur. Journal, vol. 4 No. 9, pp. 1799-1809, 1998.

(Continued)

*Primary Examiner* — Fereydoun G Sajjadi
*Assistant Examiner* — Medhanit Bahta
(74) *Attorney, Agent, or Firm* — Cook Alex Ltd.

(57) ABSTRACT

The invention provides a process for preparing 3,3,3-trifluoropropene (1243zf), the process comprising contacting a compound of formula $CX_3CH_2CH_2X$ or $CX_3CH=CH_2$, with hydrogen fluoride (HF) in the presence of a zinc/chromia catalyst, wherein each X independently is F, Cl, Br or I, provided that in the compound of formula $CX_3CH=CH_2$, at least one X is not F.

12 Claims, No Drawings

(56) References Cited

FOREIGN PATENT DOCUMENTS

| WO | WO 98/33756 | 8/1998 |
| WO | WO 98/37043 | 8/1998 |
| WO | WO 99/62857 | 12/1999 |
| WO | WO 2005/012212 A2 | 2/2005 |
| WO | WO 2005/023984 A2 | 3/2005 |
| WO | WO 2005/037743 A1 | 4/2005 |
| WO | WO 2005/037744 A1 | 4/2005 |
| WO | WO 2005/108334 A1 | 11/2005 |
| WO | WO 2006/106353 A1 | 10/2006 |
| WO | WO 2007/056194 A1 | 5/2007 |
| WO | WO 2007/079431 A2 | 7/2007 |
| WO | WO 2008/030443 A1 | 3/2008 |
| WO | WO 2008/040969 A2 | 4/2008 |
| WO | WO 2008040969 A2 * | 4/2008 |
| WO | WO 2008/054781 A1 | 5/2008 |
| WO | WO 2008/054782 A1 | 5/2008 |
| WO | WO 2008/075017 A2 | 6/2008 |
| WO | WO 2009125199 A2 | 10/2009 |
| WO | WO 2009125200 A2 | 10/2009 |
| WO | WO 2009125201 A2 | 10/2009 |
| WO | WO 2009/140563 A1 | 11/2009 |

OTHER PUBLICATIONS

Burton, et al., "Preparation of E-1,2,3,3,3-Pentafluoropropene", Journal of Fluorine Chemistry, vol. 44, pp. 167-174, 1989.

Haszeldine, et al., "Fluoro-olefins Part II—Synthesis and Reactions of Some 3: 3: 3-Trihalogenopropenes", Journal Chem. Soc., pp. 3371-3378, 1953.

Joyce, et al., "Free Radical-initiated Reaction of Ethylene with Carbon Tetrachloride", J. Am. Chemc Soc., pp. 2529-2532, 1948.

Smith, et al., Advanced Organic Chemistry, 5$^{th}$ Edition, John Wiley & Son, Inc., 2001, p. 1195.

PCT International Search Report for PCT/GB2010/000725 dated Sep. 24, 2010.

PCT Written Opinion of the International Searching Authority for PCT/GB2010/000725 dated Sep. 24, 2010.

Michael B. Smith and Jerry March, "March's Advanced Organic Chemistry Reactions, Mechanisms, and Structure", 6th Edition, ISBN 13: 978-0-471-72091-1, ISBN 10: 0-471-72091-7, Copyright 2007, John Wiley & Sons, Inc., Chapter 1: pp. 20-21; Chapter 15: pp. 1015-1016.

* cited by examiner

PROCESS FOR PREPARING 3,3,3-TRIFLUOROPROPENE

This is a National Stage of PCT Application No. PCT/GB2010/000725, which was filed on Apr. 9, 2010 and claims priority to Application No. GB0906191.2, file Apr. 9, 2009, both of which are hereby incorporated by reference.

The invention relates to a process for preparing 3,3,3-trifluoropropene.

3,3,3-trifluoropropene, which is also known as HFO-1243zf (or 1243zf), is a useful monomer for the production of fluorosilicones, and in the manufacture of trifluoropropene epoxide and 3,3,3-trifluoropropylbenzene. 1243zf is also believed to have utility in refrigerant compositions.

The listing or discussion of a prior-published document in this specification should not necessarily be taken as an acknowledgement that the document is part of the state of the art or is common general knowledge.

U.S. Pat. No. 5,986,151 describes the preparation of 1243zf starting from $CF_3CH_2CF_2H$, involving a complicated series of separate dehydrofluorination and hydrogenation reactions.

U.S. Pat. No. 4,220,608 describes the preparation of 1243zf by reacting at least one of 1,1,1,3-tetrafluoropropane (also known as 250fb), 1,1,3-trichloroprop-1-ene and 3,3,3-trichloropropene with hydrogen fluoride (HF) in the presence of a nitrogen-based catalyst. Such catalysts are not ideal, for example because they cannot easily be regenerated or separated from the reagents and/or products.

U.S. Pat. Nos. 2,889,379 and 4,465,786 both describe the preparation of 1243zf by the reaction of a halogenated hydrocarbon (e.g. 250fb) with HF in the presence of (modified) chromium oxyfluoride catalysts. The activity, selectivity, robustness and/or ease of regeneration of such catalysts is not ideal.

The subject invention addresses the above and other deficiencies in the art by the provision of a process for preparing 3,3,3-trifluoropropene (1243zf), the process comprising contacting a compound of formula $CX_3CH_2CH_2X$ or $CX_3CH=CH_2$, with hydrogen fluoride (HF) in the presence of a zinc/chromia catalyst, wherein each X independently is F, Cl, Br or I, provided that in the compound of formula $CX_3CH=CH_2$, at least one X is not F. Unless otherwise stated, this will be referred to hereinafter as the process of the invention.

In a preferred embodiment, the invention relates to the reaction of a compound of formula $CX_3CH_2CH_2X$ to produce 1243zf.

The compound of formula $CX_3CH_2CH_2X$ represents any halopropane wherein X=F, Cl, Br or I. In a preferred aspect, X=F or Cl. Examples of compounds of formula $CX_3CH_2CH_2X$ include 1,1,1,3-tetrachloropropane ($CCl_3CH_2CH_2Cl$, 250fb), 1,1,3-trichloro-1-fluoropropane ($CCl_2FCH_2CH_2Cl$), 1,3-dichloro-1,1-difluoropropane ($CClF_2CH_2CH_2Cl$), 3-chloro-1,1,1-trifluoropropane ($CF_3CH_2CH_2Cl$, 253fb) and 1,1,1,3-tetrafluoropropane ($CF_3CH_2CH_2F$, 254fb).

In one aspect, the compound of formula $CX_3CH_2CH_2X$ is selected from 250fb, 253fb and 254fb. In a preferred embodiment, the compound of formula $CX_3CH_2CH_2X$ is 253fb. In a further preferred embodiment, the compound of formula $CX_3CH_2CH_2X$ is 254fb. In a particularly preferred embodiment, the compound of formula $CX_3CH_2CH_2X$ is 250fb.

The compound of formula $CX_3CH=CH_2$ represents any halopropene wherein X=F, Cl, Br or I, provided that at least one X is not F. Preferably, X is F or Cl (provided that at least one X is not F). Examples of compounds of formula $CX_3CH=CH_2$ include 3,3,3-trichloropropene ($CCl_3CH=CH_2$), 3,3-dichloro-3-fluoropropene ($CCl_2FCH=CH_2$) and 3-chloro-3,3-difluoropropene ($CClF_2CH=CH_2$). In a preferred aspect, the compound of formula $CX_3CH=CH_2$ represents 3,3,3-trichloropropene.

The inventors have unexpectedly found that zinc/chromia catalysts are particularly effective for the fluorination and/or dehydrohalogenation reactions required by the process of the invention. In particular, the zinc/chromia catalysts are believed to be more active than other catalysts, such as chromic-based catalysts. This enables the process of the invention to be conducted using less forcing conditions (e.g. lower temperature and/or pressure) than would otherwise be necessary.

By the term "zinc/chromia catalyst" we mean any catalyst comprising chromium or a compound of chromium and zinc or a compound of zinc. Such catalysts are known in the art, see for example EP-A-0502605, EP-A-0773061, EP-A-0957074 and WO 98/10862, which are all hereby incorporated by reference. The present inventors have surprisingly found that zinc/chromia catalysts may be used promote the reaction of a compound of formula $CX_3CH_2CH_2X$ or $CX_3CH=CH_2$ (as defined herein) with HF to produce 1243zf.

Typically, the chromium or compound of chromium present in the zinc/chromia catalysts of the invention is an oxide, oxyfluoride or fluoride of chromium such as chromium oxide. The compound of formula $CX_3CH_2CH_2X$ represents any halopropane wherein X=F, Cl, Br or I. In a preferred aspect, X=F or Cl. Examples of compounds of formula $CX_3CH_2CH_2X$ include 1,1,1,3-tetrachloropropane ($CCl_3CH_2CH_2Cl$, 250fb), 1,1,3-trichloro-1-fluoropropane ($CCl_2FCH_2CH_2Cl$), 1,3-dichloro-1,1-difluoropropane ($CClF_2CH_2CH_2Cl$), 3-chloro-1,1,1-trifluoropropane ($CF_3CH_2CH_2Cl$, 253fb) and 1,1,1,3-tetrafluoropropane ($CF_3CH_2CH_2F$, 254fb).

In one aspect, the compound of formula $CX_3CH_2CH_2X$ is selected from 250fb, 253fb and 254fb. In a preferred embodiment, the compound of formula $CX_3CH_2CH_2X$ is 253fb. In a further preferred embodiment, the compound of formula $CX_3CH_2CH_2X$ is 254fb. In a particularly preferred embodiment, the compound of formula $CX_3CH_2CH_2X$ is 250fb.

The compound of formula $CX_3CH=CH_2$ represents any halopropene wherein X=F, Cl, Br or I, provided that at least one X is not F. Preferably, X is F or Cl (provided that at least one X is not F). Examples of compounds of formula $CX_3CH=CH_2$ include 3,3,3-trichloropropene ($CCl_3CH=CH_2$), 3,3-dichloro-3-fluoropropene ($CCl_2FCH=CH_2$) and 3-chloro-3,3-difluoropropene ($CClF_2CH=CH_2$). In a preferred aspect, the compound of formula $CX_3CH=CH_2$ represents 3,3,3-trichloropropene.

The inventors have unexpectedly found that zinc/chromia catalysts are particularly effective for the fluorination and/or dehydrohalogenation reactions required by the process of the invention. In particular, the zinc/chromia catalysts are believed to be more active than other catalysts, such as chromia-based catalysts. This enables the process of the invention to be conducted using less forcing conditions (e.g. lower temperature and/or pressure) than would otherwise be necessary.

By the term "zinc/chromia catalyst" we mean any catalyst comprising chromium or a compound of chromium and zinc or a compound of zinc. Such catalysts are known in the art, see for example EP-A-0502605, EP-A-0773061, EP-A-0957074 and WO 98/10862, which are all hereby incorporated by reference. The present inventors have surprisingly found that zinc/chromia catalysts may be used promote the reaction of a compound of formula $CX_3CH_2CH_2X$ or $CX_3CH=CH_2$ (as defined herein) with HF to produce 1243zf.

Typically, the chromium or compound of chromium present in the zinc/chromia catalysts of the invention is an oxide, oxyfluoride or fluoride of chromium such as chromium oxide. The total amount of the zinc or a compound of zinc present in the zinc/chromia catalysts of the invention is typically from about 0.01% to about 25%, preferably 0.1% to about 25%, conveniently 0.01% to 6% zinc, and in some embodiments preferably 0.5% by weight to about 25% by weight of the catalyst, preferably from about 1 to 10% by weight of the catalyst, more preferably from about 2 to 8% by weight of the catalyst, for example about 4 to 6% by weight of the catalyst.

In other embodiments, the catalyst conveniently comprises 0.01% to 1%, more preferably 0.05% to 0.5% zinc.

The preferred amount depends upon a number of factors such as the nature of the chromium or a compound of chromium and/or zinc or a compound of zinc and/or the way in which the catalyst is made. These factors are described in more detail hereinafter.

It is to be understood that the amount of zinc or a compound of zinc quoted herein refers to the amount of elemental zinc, whether present as elemental zinc or as a compound of zinc.

The zinc/chromia catalysts used in the invention may include an additional metal or compound thereof. Typically, the additional metal is a divalent or trivalent metal, preferably selected from nickel, magnesium, aluminium and mixtures thereof. Typically, the additional metal is present in an amount of from 0.01% by weight to about 25% by weight of the catalyst, preferably from about 0.01 to 10% by weight of the catalyst. Other embodiments may comprise at least about 0.5% by weight or at least about 1% weight of additional metal.

The zinc/chromia catalysts used in the subject invention may be amorphous. By this we mean that the catalyst does not demonstrate substantial crystalline characteristics when analysed by, for example, X-ray diffraction.

Alternatively, the catalysts may be partially crystalline. By this we mean that from 0.1 to 50% by weight of the catalyst is in the form of one or more crystalline compounds of chromium and/or one or more crystalline compounds of zinc. If a partially crystalline catalyst is used, it preferably contains from 0.2 to 25% by weight, more preferably from 0.3 to 10% by weight, still more preferably from 0.4 to 5% by weight of the catalyst in the form of one or more crystalline compounds of chromium and/or one or more crystalline compounds of zinc.

During use in a fluorination/dehydrohalogenation reaction the degree of crystallinity may change. Thus it is possible that a catalyst of the invention that has a degree of crystallinity as defined above before use in a fluorination/dehydrohalogenation reaction and will have a degree of crystallinity outside these ranges during or after use in a fluorination/dehydrohalogenation reaction.

The percentage of crystalline material in the catalysts of the invention can be determined by any suitable method known in the art. Suitable methods include X-ray diffraction (XRD) techniques. When X-ray diffraction is used the amount of crystalline material such as the amount of crystalline chromium oxide can be determined with reference to a known amount of graphite present in the catalyst (e.g. the graphite used in producing catalyst pellets) or more preferably by comparison of the intensity of the XRD patterns of the sample materials with reference materials prepared from suitable internationally recognised standards, for example NIST (National Institute of Standards and Technology) reference materials.

The zinc/chromia catalysts typically have a surface area of at least 50 $m^2/g$ and preferably from 70 to 250 $m^2/g$ and most preferably from 100 to 200 $m^2/g$ before it is subjected to pre-treatment with a fluoride containing species such as hydrogen fluoride or a fluorinated hydrocarbon. During this pre-treatment, which is described in more detail hereinafter, at least some of the oxygen atoms in the catalyst are replaced by fluorine atoms.

The zinc/chromia catalysts of the invention typically have an advantageous balance of levels of activity and selectivity. Preferably, they also have a degree of chemical robustness that means that they have a relatively long working lifetime. The zinc/chromia catalysts preferably also have a mechanical strength that enables relatively easy handling, for example they may be charged to reactors or discharged from reactors using known techniques.

The zinc/chromia catalysts may be provided in any suitable form known in the art. For example, they may be provided in the form of pellets or granules of appropriate size for use in a fixed bed or a fluidised bed. The catalysts may be supported or unsupported. If the catalyst is supported, suitable supports include $AlF_3$, fluorinated alumina or activated carbon.

The zinc/chromia catalysts include promoted forms of such catalysts, including those containing enhanced Lewis and/or Brönsted acidity and/or basicity.

The amorphous catalysts which may be used in the subject invention can be obtained by any method known in the art for producing amorphous chromia-based catalysts. Suitable methods include co-precipitation from solutions of zinc and chromium nitrates on the addition of ammonium hydroxide. Alternatively, surface impregnation of the zinc or a compound thereof onto an amorphous chromia catalyst can be used.

Further methods for preparing the amorphous zinc/chromia catalysts include, for example, reduction of a chromium (VI) compound, for example a chromate, dichromate, in particular ammonium dichromate, to chromium (III), by zinc metal, followed by co-precipitation and washing; or mixing as solids, a chromium (VI) compound and a compound of zinc, for example zinc acetate or zinc oxalate, and heating the mixture to high temperature in order to effect reduction of the chromium (VI) compound to chromium (III) oxide and oxidise the compound of zinc to zinc oxide.

The zinc may be introduced into and/or onto the amorphous chromia catalyst in the form of a compound, for example a halide, oxyhalide, oxide or hydroxide depending at least to some extent upon the catalyst preparation technique employed. In the case where amorphous catalyst preparation is by impregnation of a chromia, halogenated chromia or chromium oxyhalide, the compound is preferably a water-soluble salt, for example a halide, nitrate or carbonate, and is employed as an aqueous solution or slurry. Alternatively, the hydroxides of zinc and chromium may be co-precipitated (for example by the use of a base such as sodium hydroxide or ammonium hydroxide) and then converted to the oxides to prepare the amorphous catalyst. Mixing and milling of an insoluble zinc compound with the basic chromia catalyst provides a further method of preparing the amorphous catalyst precursor. A method for making amorphous catalyst based on chromium oxyhalide comprises adding a compound of zinc to hydrated chromium halide.

The amount of zinc or a compound of zinc introduced to the amorphous catalyst precursor depends upon the preparation method employed. It is believed that the working catalyst has a surface containing cations of zinc located in a chromium-containing lattice, for example chromium oxide, oxyhalide, or halide lattice. Thus, the amount of zinc or a compound of zinc required is generally lower for catalysts made by impregnation than for catalysts made by other methods such as co-precipitation, which also contain the zinc or a compound of zinc in non-surface locations.

Any of the aforementioned methods, or other methods, may be employed for the preparation of the amorphous catalysts which may be used in the process of the subject invention.

The zinc/chromia catalysts described herein are typically stabilised by heat treatment before use such that they are stable under the environmental conditions that they are exposed to in use. This stabilisation is often a two-stage process. In the first stage, the catalyst is stabilised by heat treatment in nitrogen or a nitrogen/air environment. In the art, this stage is often called "calcination". Fluorination catalysts are then typically stabilised to hydrogen fluoride by heat treatment in hydrogen fluoride. This stage is often termed "pre-fluorination".

By careful control of the conditions under which these two heat treatment stages are conducted, crystallinity can be induced into the catalyst to a controlled degree.

For example, an amorphous catalyst may be heat treated at a temperature of from about 300 to about 600° C., preferably from about 400 to 600° C., more preferably from 500 to 590° C., for example 520, 540, 560 or 580° C. for a period of from about 1 to about 12 hours, preferably for from about 2 to about 8 hours, for example about 4 hours in a suitable atmosphere. Suitable atmospheres under which this heat treatment can be conducted include an atmosphere of nitrogen or an atmosphere having an oxygen level of from about 0.1 to about 10% v/v in nitrogen. Other oxidizing environments could alternatively be used. For example, environments containing suitable oxidizing agents include, but are not limited to, those containing a source of nitrate, $CrO_3$ or $O_2$ (for example air). This heat treatment stage can be conducted in addition to or instead of the calcining stage that is typically used in the prior art to produce amorphous catalysts.

Conditions for the pre-fluorination stage can be selected so that they do not substantially introduce crystallinity into the catalyst. This may be achieved by heat treatment of the catalyst precursor at a temperature of from about 200 to about 500° C., preferably from about 250 to about 400° C. at atmospheric or super atmospheric pressure for a period of from about 1 to about 16 hours in the presence of hydrogen fluoride, optionally in the presence of another gas such as nitrogen.

Conditions for the pre-fluorination stage can be selected so that they induce a change in the crystallinity of the catalyst or so that they do not induce such a change. The present inventors have found that heat treatment of the catalyst precursor at a temperature of from about 250 to about 500° C., preferably from about 300 to about 400° C. at atmospheric or super atmospheric pressure for a period of from about 1 to about 16 hours in the presence of hydrogen fluoride, optionally in the presence of another gas such as air, can produce a catalyst in which the crystallinity is as defined above, for example from 0.1 to 8.0% by weight of the catalyst (typically from 0.1 to less than 8.0% by weight of the catalyst) is in the form of one or more crystalline compounds of chromium and/or one or more crystalline compounds of the at least one additional metal.

The skilled person will appreciate that by varying the conditions described above, such as by varying the temperature and/or time and/or atmosphere under which the heat treatment is conducted, the degree of crystallinity of the catalyst may be varied. Typically, for example, catalysts with higher degrees of crystallinity (e.g. from 8 to 50% by weight of the catalyst) may be prepared by increasing the temperature and/or increasing the calcination time and/or increasing the oxidising nature of the atmosphere under which the catalyst pre-treatment is conducted.

The variation of catalyst crystallinity as a function of calcination temperature, time and atmosphere is illustrated by the following table showing a series of experiments in which 8 g samples of a 6% zinc/chromia catalyst were subjected to calcination across a range of conditions and the level of crystallinity induced determined by X-Ray diffraction.

| Calcination Time (t, hrs) | Calcination Temperature (T, ° C.) | Atmosphere nitrogen:air (D, v/v) | % Cryst $Cr_2O_3$ Content |
|---|---|---|---|
| 4 | 400.0 | 15 | 1 |
| 4 | 400.0 | 15 | 1 |
| 2 | 450.0 | 20 | 9 |
| 6 | 350.0 | 20 | 0 |
| 2 | 450.0 | 10 | 18 |
| 2 | 350.0 | 10 | 0 |
| 6 | 450.0 | 20 | 20 |
| 6 | 350.0 | 10 | 0 |
| 6 | 450.0 | 10 | 30 |
| 4 | 400.0 | 15 | 1 |
| 2 | 350.0 | 20 | 0 |

The pre-fluorination treatment typically has the effect of lowering the surface area of the catalyst. After the pre-fluorination treatment the catalysts of the invention typically have a surface area of 20 to 200 $m^2$/g, such as 50 to 150 $m^2$/g, for example less than about 100 $m^2$/g.

In use, the zinc/chromia catalyst may be regenerated or reactivated periodically by heating in air at a temperature of from about 300° C. to about 500° C. Air may be used as a mixture with an inert gas such as nitrogen or with hydrogen fluoride, which emerges hot from the catalyst treatment process and may be used directly in fluorination processes employing the reactivated catalyst. Alternatively, the catalyst can be regenerated continuously whilst in use by introducing an oxidising gas into the reactor e.g. oxygen or chlorine.

The zinc/chromia catalyst may be used in the process of the invention in an amount of from about 0.01 to about 50% by weight, such as from 0.1 to about 30%, for example from about 0.5 to about 20%, based on the combined weight of organics (e.g. compound of formula $CX_3CH_2CH_2X$ or $CX_3CH=CH_2$) and HF.

The process of the invention can be carried out in any suitable apparatus, such as a static mixer, a stirred tank reactor or a stirred vapour-liquid disengagement vessel. Preferably, the apparatus is made from one or more materials that are resistant to corrosion, e.g. Hastelloy® or Inconel®.

The process of the invention may be carried out batch-wise or (semi-)continuously. Preferably, the process of the invention is carried out continuously. Typically, the process of the invention is carried out in the vapour phase.

The process may be carried out at atmospheric, sub- or super atmospheric pressure, typically at from 0 to about 30 bara, preferably from about 1 to about 20 bara.

Typically, the process of the invention is carried out a temperature of from about 100° C. to about 500° C. (e.g. from about 150° C. to about 500° C. or about 100 to about 450° C.). Preferably, the process is conducted at a temperature of from about 150° C. to about 450° C., such as from about 150° C. to about 400° C., e.g. from about 200° C. to about 350° C. Lower temperatures may also be used in the process of the invention, for example in the conversion of 250fb to 1243zf, such as from about 150° C. to about 350° C., e.g. from about 150° C. to about 300° C. or from about 150° C. to about 250° C.

The process of the invention typically employs a molar ratio of HF:organics of from about 1:1 to about 100:1, such as from about 3:1 to about 50:1, e.g. from about 4:1 to about 30:1 or about 5:1 or 6:1 to about 20:1 or 30:1.

The reaction time for the process of the invention generally is from about 1 second to about 100 hours, preferably from about 10 seconds to about 50 hours, such as from about 1 minute to about 10 or 20 hours. In a continuous process, typical contact times of the catalyst with the reagents are from about 1 to about 1000 seconds, such from about 1 to about 500 seconds or about 1 to about 300 seconds or about 1 to about 50, 100 or 200 seconds.

The process of the invention is particularly effective for preparing 3,3,3-trifluoropropene (1243zf) by contacting 1,1,1,3-tetrachloropropane (250fb) with hydrogen fluoride (HF) in the presence of a zinc/chromia catalyst.

250fb may be purchased from common suppliers of halogenated hydrocarbons, such as Apollo Scientific, Stockport, UK. Alternatively, 250fb may be prepared by the telomerisation of carbon tetrachloride ($CCl_4$) and ethylene (see, for example, J. Am. Chem. Soc. Vol. 70, p 2529, 1948, which is incorporated herein by reference).

The conversion of 250fb to 1243zf typically involves fluorination and dehydrohalogenation sub-steps.

For example, 250fb may be fluorinated to produce a compound of formula $CX_3CH_2CH_2Cl$ (wherein X=Cl or F), as illustrated in the scheme below. 1243zf may be produced by a final dehydrochlorination step of the compound of formula $CX_3CH_2CH_2Cl$ wherein X=F. This is illustrated below as route (a).

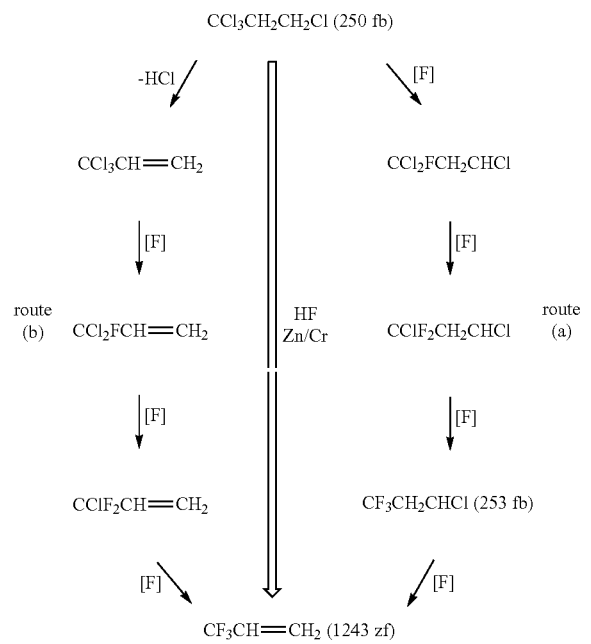

Alternatively, 250fb may be dehydrochlorinated to produce 3,3,3-trichloropropene, followed by step-wise fluorination to produce 1243zf. This is illustrated above as route (b).

Either or both routes (a) and (b) may be operable to convert 250fb to 1243zf. For example, $CCl_2FCH_2CHCl$ in route (a) may be dehydrochlorinated to produce $CCl_2FCH=CH_2$ in route (b). It is anticipated that some of these reactions may occur spontaneously if HF and 250fb are mixed at elevated temperatures, but the reaction will not go to completion in the absence of a zinc/chromia catalyst in any reasonable timescale.

Surprisingly, the inventors have found that zinc/chromia catalysts are effective at facilitating the one-pot conversion of 250fb and HF to 1243zf. In particular, the activity of the catalyst is believed to allow less forcing conditions (e.g. lower temperatures) compared to known (vapour phase) processes for producing 1243zf, whilst maintaining excellent conversion of 250fb and selectivity to 1243zf.

The invention will now be illustrated with the following non-limiting examples.

EXAMPLE 1

Hydrofluorination of 250fb ($CCl_3CH_2CH_2Cl$) at Elevated Pressure

The reactor, made from an Inconnel tube 30 cm×0.5 inches, was charged with 6 g of a 5.2% Zn/Chromia catalyst, which was essentially amorphous in character, and was treated as follows:

The catalyst was first dried by heating under nitrogen (80 ml/min) at 250° C. and 3 berg for 48 hours. Next, pre-fluorination of the catalyst was begun by introducing HF (4 ml/min) into the nitrogen stream and increasing the temperature to 300° C. for 16 hours. During the last 5 hours the nitrogen flow was reduced steadily to zero. The temperature was then ramped to 380° C. at 25° C./hr and held at 380° C. for 7 hours and then cooled to 250° C. at 25° C./hr.

A feed mixture comprising 250fb (3 ml/min) and HF (45 ml/min) was then passed over the catalyst at 15 barg and 200° C. The gases exiting the reactor were periodically sampled and analysed by GC after passing through an alkaline scrubber to remove acid gases. The only products detected in the reactor off-gases following removal of the acid gases were the desired product 1243zf (91 mol %, $CF_3CH=CH_2$) and 1,1-difluoro-1,3-dichloropropane (9 mol %, $CF_2ClCH_2CH_2Cl$).

It is believed that the 1,1-difluoro-1,3-dichloropropane could be converted to 1243zf by altering the reaction conditions (e.g. by increasing the temperature and/or contact time). In this way, 250fb could be fully converted in 100% selectivity to 1243zf in a single pass.

EXAMPLE 2

Hydrofluorination of 250fb ($CCl_3CH_2CH_2Cl$) at Atmospheric Pressure

The reactor, made from an Inconnel tube 30 cm×0.5 inches, was loaded with 2.0 g of a 5.2% wt Zn on chromia catalyst which was essentially amorphous in character. The catalyst was then dried under nitrogen (80 ml/min) at 250° C. for 3 hours. HF (20 ml/min) was then introduced into the nitrogen flow and pre-fluorination of the catalyst commenced. When HF was detected in the reactor off-gases the reactor temperature was ramped from 250° C. to 370° C. at 25° C./hr and maintained there for 7 hours before being cooled back to 200° C. at 25° C./hr.

A feed mixture comprising 250fb (1 ml/min), HF (25 ml/min) and nitrogen (30 ml/min) was fed to the reactor at 200° C. for a total of 15 hours. The gases exiting the reactor were scrubbed with an alkaline solution to remove acid gases and analysed by GC-MS and GC. The only species identified in the scrubbed reactor off-gases throughout the whole experiment was 1243zf.

Examples 1 and 2 demonstrate that the reaction of 250fb with HF using a zinc/chromia catalyst selectively produces 1243zf under very mild conditions.

EXAMPLE 3

Vapour Phase Conversion of 254fb ($CF_3CH_2CH_2F$) to 1243zf ($CF_3CH=CH_2$)

The reactor, made from an Inconnel tube 30 cm×0.5 inches was loaded with 2.0 g of a 5.2% wt Zn on chromia catalyst which was essentially amorphous in character. The catalyst was then dried under nitrogen (80 ml/min) at 250° C. for 3 hours. HF (20 ml/min) was then introduced into the nitrogen flow and pre-fluorination of the catalyst commenced. When HF was detected in the reactor off-gases the reactor temperature was ramped from 250° C. to 370° C. at 25° C./hr and maintained there for 7 hours before being cooled back to 200° C. at 25° C./hr.

Mixtures of HF and 254fb were then fed across the catalyst at various temperatures and ratio's to demonstrate the conversion of 254fb to 1243zf. Nitrogen carrier gas flows were used to aid delivery of the feeds to the reactor. The gases exiting the reactor were analysed by GC-MS and GC. The results are summarised in the Table below:

| | Temperature (° C.) | | | | | | | | | | |
|---|---|---|---|---|---|---|---|---|---|---|---|
| | 200 | 225 | 250 | 200 | 225 | 250 | 275 | 300 | 300 | 225 | 250 |
| 254fb feed (ml/min) | 13.5 | 12.1 | 16.7 | 20.4 | 22.9 | 10.6 | 12.8 | 10.0 | 1.0 | 4.9 | 4.9 |
| HF feed (ml/min) | 27.9 | 27.9 | 27.6 | 34.3 | 35.3 | 35.4 | 35.2 | 35.6 | 35.3 | 0 | 0 |
| Ratio HF:254fb | 2.1 | 2.3 | 1.7 | 1.7 | 1.5 | 3.3 | 2.8 | 3.6 | 35.4 | N/A | N/A |
| Total $N_2$ flow (ml/min) | 10.1 | 10.1 | 10.1 | 10.1 | 10.1 | 10.1 | 10.1 | 10.1 | 10.1 | 5 | 5 |
| ROG* 254fb (mol %) | 93.3 | 50.1 | 14.8 | 93.3 | 71.9 | 17.4 | 1.5 | 0.1 | 0.7 | 1.3 | 0.1 |
| ROG* 1243zf (mol %) | 6.7 | 49.9 | 85.2 | 6.7 | 28.1 | 82.6 | 98.5 | 99.9 | 99.3 | 98.7 | 99.9 |

*ROG = Reactor Off-gas composition

As can be seen the conversion of 254fb to 1243xf is clean and facile over a zinc/chromia catalyst at moderate conditions.

The invention claimed is:

1. A process for preparing 3,3,3-trifluoropropene (1243zf), the process comprising contacting $CCl_3CH_2CH_2Cl$ (250fb) with hydrogen fluoride (HF) in the presence of a zinc/chromia catalyst, wherein the zinc/chromia catalyst is amorphous or from 0.1 to 50% by weight of the zinc/chromia catalyst is in the form of one or more crystalline compounds of chromium and/or one or more crystalline compounds of zinc, wherein the zinc/chromia catalyst contains from about 4 to about 25% by weight of a compound of zinc, and wherein the catalyst contains (i) chromium or a compound of chromium, and (ii) a compound of zinc.

2. A process according to claim 1 wherein the process is conducted at a temperature of from about 100° C. to about 500° C.

3. A process according to claim 1 wherein the process is conducted at a pressure of from 0 to about 30 bara.

4. A process according to claim 1 wherein the molar ratio of HF:$CCl_3CH_2CH_2Cl$ (250fb) is from about 1:1 to about 100:1.

5. A process according to claim 1 wherein the process is conducted in the vapour phase.

6. A process according to any of the preceding claims wherein the process is continuous or semi-continuous.

7. A process according to claim 1 wherein the process is conducted at a temperature of from about 150° C. to about 450° C.

8. A process according to claim 1 wherein the process is conducted at a pressure of from about 1 to about 20 bara.

9. A process according to claim 1 wherein the molar ratio of HF:$CCl_3CH_2CH_2Cl$ (250fb) is from about 3:1 to about 50:1.

10. A process according to claim 1 wherein 0.2 to 25% by weight of the zinc/chromia catalyst is in the form of one or more crystalline compounds of chromium and/or one or more crystalline compounds of zinc.

11. A process according to claim 1 wherein the zinc/chromia does not contain an additional metal.

12. A process according to claim 1 wherein the zinc/chromia catalyst is prepared by co-precipitation of a compound of chromium with a compound of zinc.

* * * * *